United States Patent
Cassoni et al.

(10) Patent No.: US 6,887,226 B2
(45) Date of Patent: May 3, 2005

(54) SEWN DIGITAL TAMPON

(75) Inventors: Robert Paul Cassoni, Centerville, OH (US); Dale Edwin Barker, Hamilton, OH (US)

(73) Assignee: The Procter & Gamble Company, Cincinnati, OH (US)

(*) Notice: Subject to any disclaimer, the term of this patent is extended or adjusted under 35 U.S.C. 154(b) by 332 days.

(21) Appl. No.: 10/161,484

(22) Filed: May 31, 2002

(65) Prior Publication Data

US 2003/0225389 A1 Dec. 4, 2003

(51) Int. Cl.[7] .............................................. A61F 13/20
(52) U.S. Cl. .............................. 604/385.18; 604/904
(58) Field of Search .......................... 604/385.18, 904

(56) References Cited

U.S. PATENT DOCUMENTS

| | | | |
|---|---|---|---|
| 2,715,374 A | * | 8/1955 | Carrier .................. 112/470.22 |
| 3,732,866 A | * | 5/1973 | Accavallo ................... 604/379 |
| 3,749,094 A | | 7/1973 | Duncan |
| 3,762,413 A | * | 10/1973 | Hanke ......................... 604/15 |
| 3,766,921 A | | 10/1973 | Dulle |
| 3,794,029 A | | 2/1974 | Dulle |
| 3,812,856 A | | 5/1974 | Duncan et al. |
| 3,814,469 A | | 6/1974 | Simon |
| 3,815,601 A | | 6/1974 | Schaefer |
| 3,834,389 A | | 9/1974 | Dulle |
| 3,852,847 A | | 12/1974 | Etz |
| 3,856,013 A | | 12/1974 | Dulle |
| 3,863,636 A | | 2/1975 | Johnson |
| 3,948,257 A | | 4/1976 | Bossak |
| 3,965,905 A | | 6/1976 | Schoenholz et al. |
| 3,970,022 A | | 7/1976 | Kopatz et al. |
| 3,976,075 A | | 8/1976 | Chinai et al. |
| 4,169,004 A | | 9/1979 | Kock et al. |
| 4,332,251 A | | 6/1982 | Thompson |
| 4,475,911 A | | 10/1984 | Gellert |
| 4,490,896 A | * | 1/1985 | Small .................... 29/890.031 |
| 4,699,618 A | | 10/1987 | Sustmann |
| 4,923,440 A | | 5/1990 | Genaro |
| 5,084,038 A | | 1/1992 | Sheldon et al. |
| 5,370,633 A | | 12/1994 | Villalta |
| 5,383,891 A | | 1/1995 | Walker |
| 5,395,308 A | | 3/1995 | Fox et al. |
| 5,458,589 A | | 10/1995 | Comin-DuMong |
| 5,533,990 A | | 7/1996 | Yeo |
| 5,542,914 A | | 8/1996 | Van Iten |
| 5,566,435 A | | 10/1996 | Brown, Jr. |
| 5,659,934 A | | 8/1997 | Jessup et al. |
| 5,674,239 A | | 10/1997 | Zadini et al. |
| 5,738,646 A | | 4/1998 | Fox et al. |
| 5,827,256 A | | 10/1998 | Balzar |
| 5,873,971 A | | 2/1999 | Balzar |
| 5,891,123 A | | 4/1999 | Balzar |
| 6,142,984 A | | 11/2000 | Brown et al. |
| 6,312,419 B1 | | 11/2001 | Durel-Crain |

* cited by examiner

*Primary Examiner*—Larry I. Schwartz
*Assistant Examiner*—C. Lynne Anderson
(74) *Attorney, Agent, or Firm*—Ingrid N. Hickman (57) ABSTRACT

A tampon pledget having a top end, a bottom end, a first side end, a second side end, and a central portion between the first side end and the second side end. A first cord and a second cord are attached to the central portion. The first cord and the second cord lie in parallel planes.

10 Claims, 7 Drawing Sheets

SEWN DIGITAL TAMPON

FIELD OF THE INVENTION

This invention relates to a sewn digital tampon.

BACKGROUND OF THE INVENTION

The invention relates to a digital tampon for feminine hygiene with a withdrawal cord. The digital tampon is formed from a tampon pledget.

Catamenial tampons comprised of absorbent material compressed to cylindrical form and provided with a withdrawal string attached to a rear portion of the tampon are presently being marketed in three major styles. One style generally known as the tube type tampon uses a pair of telescoping tubes as an insertion device. In this type, the tampon is disposed in the front end of the outer tube of a pair of telescopically associated tubes and the withdrawal string is extended to substantially its full length through the hollow center of the inner tube. The entire assembly is enclosed in a removable wrapper for hygienic handling.

A second style, generally known as the stick type tampon uses a stick as the insertion device. In this type an elongated inserter stick is removably disposed in a socket extending into the base of the tampon and the withdrawal string is extended to substantially its full length in an area parallel to the stick. This entire assembly is also enclosed in a removable wrapper for hygienic handling.

A third style known as the digital type tampon has no insertion device associated with it. For this type there are a number of ways suggested for insertion of the digital tampon. Namely, the digital tampon is introduced into the body cavity by hand, without an introduction aid where the user often uses the looped withdrawal string as an aid.

For tampons with an insertion device, the withdrawal string typically comprises a single cord that is sewn to the tampon pledget. The cord comprising the withdrawal cord tend to be of larger diameter to sufficiently sew the cord to the pledget using traditional techniques. Narrower or thinner cords are difficult to sew securely to a pledget without overstitching. Another problem in sewing narrower or thinner cords is the needle missing the cord entirely which results in less cord attachment to the tampon pledget. Secure attachment or engagement of the withdrawal string to or around the tampon is of high importance so that there is no inadvertent detachment of the withdrawal string from the tampon while attempting to remove the tampon from the body—which would leave no easy means for removing a tampon from the body and may require the assistance of medical personnel.

The intent of a withdrawal string is that a portion or end of the withdrawal string remain outside the body for easy grasping while another end of the withdrawal string is secured to the tampon. For digital tampons, looped withdrawal cords are typically used. The withdrawal cord is looped around the tampon pledget and a portion of the loop remains outside the body. This means that instead of one, there are often two cord segments outside the body which then pass by the labia, through the introitus and into the vaginal cavity where they are engaged with the tampon.

The withdrawal string for a digital tampon is typically narrower than those used with other tampons, partly because of the doubling of material passing through the body would lead to a more uncomfortable feeling for the wearer if thicker cords were employed. To securely engage the thinner cords or cord segments of the thinner withdrawal string with the tampon, manufacturers typically loop the withdrawal string through a hole punched into the tampon pledget or loop it around the tampon pledget by passing the pledget through the loop then folding or rolling the pledget about the looped withdrawal cord one or more times.

A more preferred way to engage a withdrawal string to a tampon is by sewing the cord or cord segment to the pledget. In the single cord tampons with insertion devices, the thread is either sewn through the cord and into the pad or sewn over the cord into the pad essentially encapsulating the cord using a sewing machine. It is preferred to sew the thread through the cord into a tampon pledget. The typical process for sewing a cord to a pledget is similar to the practice for sewing decorative cording to fabric as part of a decorative garment manufacture. The typical pledget process for sewing involves a presser foot and sewing table whereupon the pledget and the cord are combined between the presser foot and horizontal sewing support surface or table such that a needle loaded with thread can enter and withdraw from the advancing cord and pad such that a stitch is formed by the up-and-down (or in-and-out) motion of the needle engaging the top sewing thread with the looper thread introduced below the pledget and cord from underneath the sewing table. The cord is introduced to the pad under the presser foot with the cord traveling from above the presser foot then traveling through or under the bottom plane of the presser foot by the cord turning about a turning surface with an axis that is perpendicular to the axis/plane (typically a vertical axis/plane) through which the needle motion travels during the stitching cycle. Often there are lateral motion guides (such as aperture or slot side walls/surfaces or vertical pin guides) to minimize the lateral travel of the cord as it enters under the pressing foot in an attempt to center the cord underneath the needle. The current lateral guides provide some assistance, but there is still variation that becomes more unacceptable as the width or diameter of the cord decreases. From the turning surface to the closest stitch where the cord is sewn to the pledget, there is an inducing tension within the cord between those two points.

This application is directed to the digital sewn digital type tampon, and is particularly directed to an improved arrangement for the attachment of the string to the tampon pledget which provides easier facilitation of introducing the digital tampon into the body cavity.

SUMMARY OF THE INVENTION

A tampon pledget having a top end, a bottom end, a first side end, a second side end, and a central portion between the first side end and the second side end. The central portion has a first cord and a second cord attached thereto. The first cord and the second cord lie in parallel planes. The first cord and the second cord, may be attached to the pledget by sewing a thread through the first cord, the second cord, and the pledget.

All documents cited are, in relevant part, incorporated herein by reference; the citation of any document is not to be construed as an admission that it is prior art with respect to the present invention.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

The present invention provides a new and improved digital tampon article as well as method of making a digital tampon with a sewn cord, in particular digital tampons with more than one cord segment often comprising a loop. Further, the method provides an improved process for sewing one or more cords or decorative cords not only to tampon pledgets, but also to fabrics and garment when producing decorative garments.

Section A will provide terms which will assist the reader in best understanding the features of the invention and not to introduce limitations in the terms inconsistent with the context in which they are used in this specification. Theses definitions are not intended to be limiting. Section B will discuss the digital tampon that results from the method of making the digital tampon. Section C will discuss the apparatus used to make the digital tampon. Section D will discuss the different stages of the method of manufacturing a digital tampon.

A. Terms

In general in this specification, the term "tampon" is used to refer to a finished tampon after the compression process referred to below. As used herein the term "tampon" refers to any type of absorbent structure that is inserted into the vaginal canal or other body cavities for the absorption of fluid therefrom. Typically, tampons are constructed from an absorbent material that has been compressed in one or more steps employing one or more parts of the absorbent material in the radial direction, axially along the longitudinal and lateral axes or in both the radial and axial directions to provide a tampon, which is of a size and stability to allow insertion within the vagina or other body cavity. A tampon that has been so compressed is referred to herein as a "self-sustaining" form. The term "self-sustaining" is defined below.

As used herein, "self-sustaining" is a measure of the degree or sufficiency to which the tampon retains the compression applied to the absorbent material of the tampon pledget such that in the subsequent absence of the external forces, the resulting tampon will tend to retain its general shape and size. It will be understood by one of skill in the art that this self-sustaining form need not, and preferably does not persist during actual use of the tampon. That is, once the tampon is inserted and begins to acquire fluid, the tampon will begin to expand and may lose its self-sustaining form.

The term "digital tampon" refers to a tampon which is intended to be inserted into the vaginal canal with the user's finger and without the aid of an applicator. Thus, digital tampons are typically visible to the consumer prior to use rather than being housed in an applicator.

As used herein the terms "pledget" or "tampon pledget" are intended to be interchangeable and refer to a construction of absorbent material prior to the compression of such construction into a tampon as described above. Tampon pledgets are sometimes referred to as a tampon blank, or a softwind, or a pad, and the term "pledget" is intended to include such terms as well.

As used herein the terms "vaginal cavity," "within the vagina," and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina) and the cervix and is not intended to include the interlabial space, including the floor of vestibule. The externally visible genitalia generally is not included within the term "vaginal cavity" as used herein. As used herein, "vaginally insertable shape" refers to the geometrical form of the absorbent tampon after compression. While not to be limited to such dimensions, a typical compressed tampon for human use is 10–16 millimeters wide and 30–60 millimeters long depending on absorbency. For other mammals, typical tampon dimensions may vary based on differences in vaginal cavity geometry. While the tampon may be compressed into a substantially cylindrical configuration, other shapes are possible. These may include shapes having a cross section or cross-section element that may be described as rectangular, triangular, trapezoidal, semi-circular, hourglass, or other suitable shapes.

The term "thread" refers to a filament, a group of filaments often twisted together with an actual twist or false-twist arrangement, or a filamentous length formed by spinning and twisting short textile fibers into a continuous strand or a filamentous-like length drawn from a reservoir of material such as a polymeric resin. The composition of the components of a thread can be made from animal, plant, mineral or man-made origin. Example material compositions include cotton, cellulose, rayon, polyolefins such as polyethylene or polypropylene, nylon, silk, Dacron (Registered), etc; though preferred compositions include cotton, rayon or polypropylene. Thread can be used by itself in a sewing process used in combination with a needle to help unite or fasten materials together via stitches such as by weaving or passing through materials to or the thread can be used by itself to help reinforce a material or close a section of material such as a fabric. Alternatively, thread can be a component of a larger width material such as a cord or a fabric.

The term "yarn" refers to a continuous often plied strand composed of fibers or filaments.

The term "cord" refers to a long or slender flexible material often employed to transmit tensile forces, such as would be needed during typical tampon withdrawal from the body. Cord cross-sections are often circular however they can take any shape depending on the form of the cord. Small width cords are commonly referred to as strings while much larger width cords can be referred to as ropes. A cord can be comprised of single or usually multiple filaments or strands (such as of yarn or thread) woven or twisted or false-twisted together. Withdrawal cords useful in the present invention may be made of any suitable material known in the prior art and include cotton and rayon. For the purposes of this development, a cord can also comprise a material from a strip of material resembling a tape, a ribbon, a soutache, or a braid, of which they can be made from nonwoven, woven, resin, extruded, solvent drawn, melt drawn, monofilamentous, or film-based components. Example material compositions include cotton, cellulose, rayon, polyolefins such as polyethylene or polypropylene, nylon, silk, Dacron (Registered), etc; though preferred compositions include cotton, rayon or polypropylene. Tampon cords can range from 0.05 millimeters to 0.8 millimeters.

The term "cord segment" refers to a portion of the length of a cord which can comprise multiple segments or portions wherein the segments or portions are connected, either integrally or by joining means (e.g. a knot), to at least one other cord segment or portion of a cord. The length of a cord segment can be any length as long as it is greater than zero and less than the total length of the entire cord. Cord segment lengths can vary and be defined in relation to the situation, though typically cord segments of interest for tampons range from 0.1 inches to 2 inches (2.54 mm to 50.8 mm) in length.

The term "withdrawal cord" or "withdrawal string" refers to one or more cords or cord segments attached to the tampon to permit ease for removing the tampon from the body.

The abbreviation "mm" is millimeter.

B. Digital Tampon of the Present Invention

Figure 1:
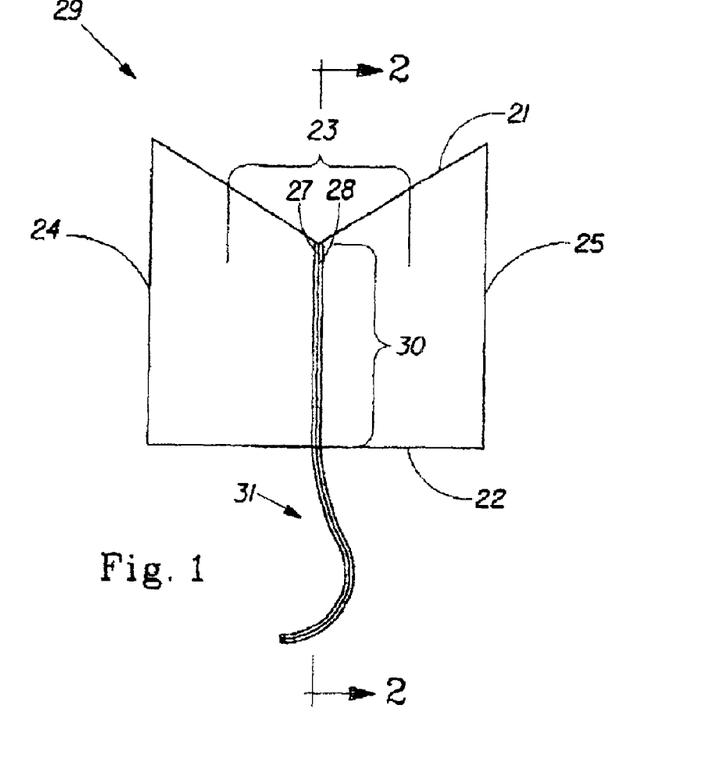
FIG. 1 is a plan view of a sewn tampon pledget.

Referring to FIG. 1, the tampon pledget has a top end 21, a bottom end 22, a first side end 24, a second side end 25, and a central portion 23 between the first side end 24 and the second side end 25. A first cord 26 (not shown in FIG. 1) and a second cord 27 are attached to the central portion 23. The first cord 26 and the second cord 27 lie in parallel planes.

Figure 2:
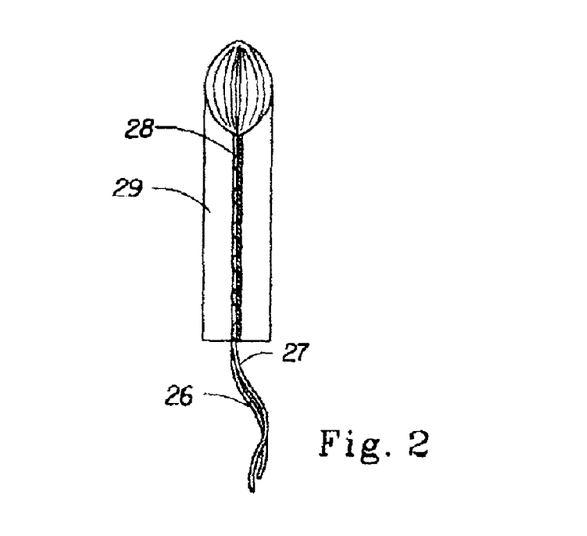
FIG. 2 is a cross-section view along the lines 2—2 of the sewn tampon pledget.
Figure 3:
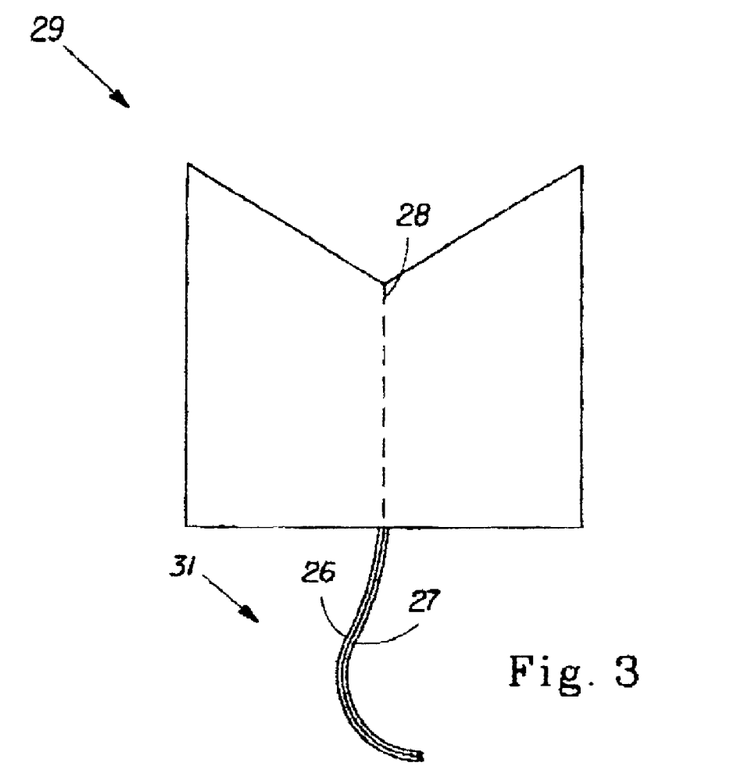
FIG. 3 is a back view of the sewn tampon pledget.

Referring primarily to FIG. 2., a thread 28 is sewn through at least a portion of the first cord 26, the second cord 27, and the pledget 29. The first cord 26 and the second cord 27 can be attached to the central portion 23 by other means known in the art such as gluing, heat setting, etc. Referring to FIG. 1, the first cord 26 and the second cord 27 have an attached portion 30 and a tail portion 31. The attached portion 30 lies between the top end 21 and the bottom end 22. The tail portion 31 extends beyond the bottom end 22. The tail portion 31 consists of the first cord 26 and the second cord 27. The first cord 26 and the second cord 27 can be used to assist the user during the insertion of the digital tampon and assist the user in withdrawing the digital tampon from the woman's vagina.

Figure 8:
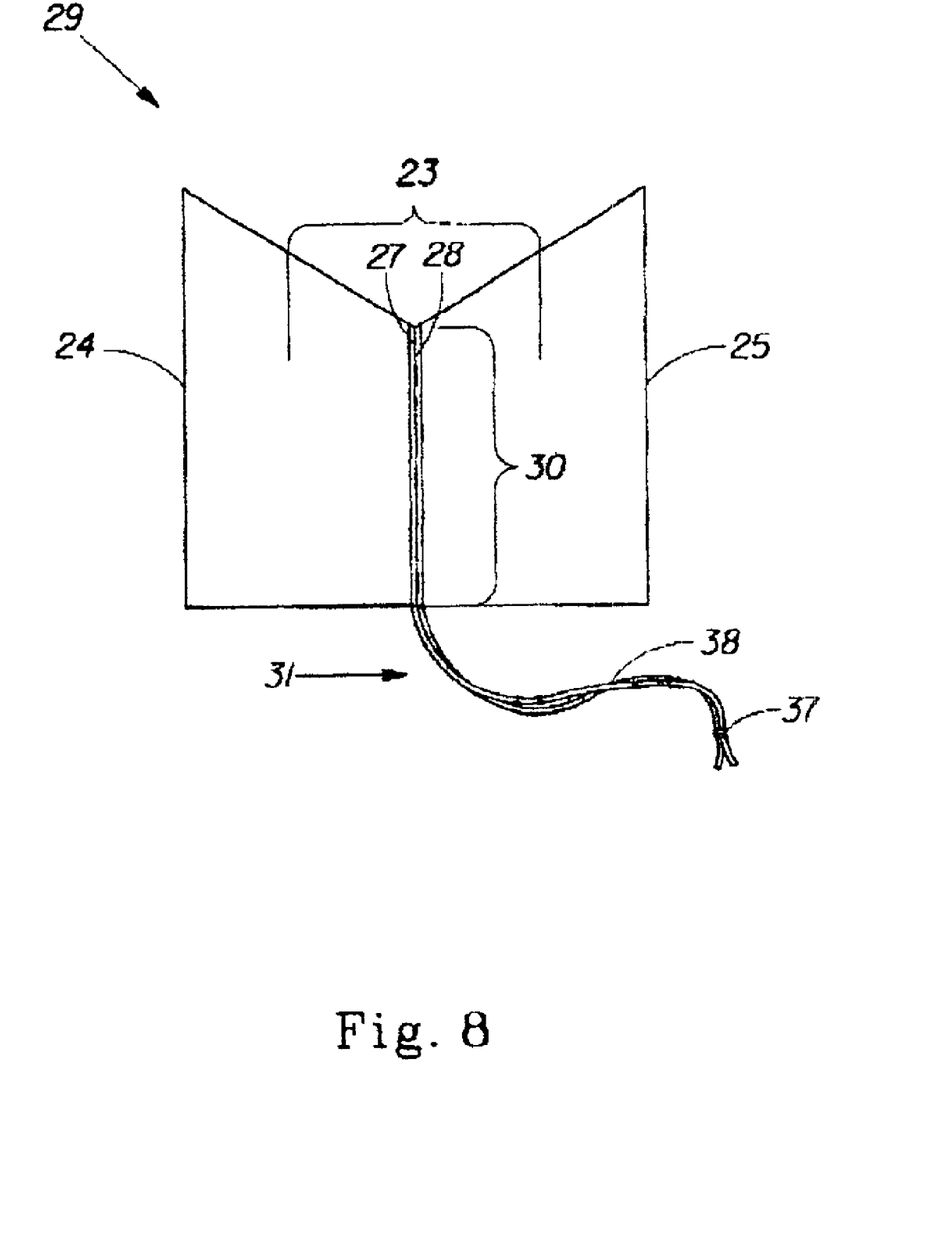
FIG. 8 is a perspective front view of a sewn tampon pledget with the first cord and the second knotted.
Figure 9:
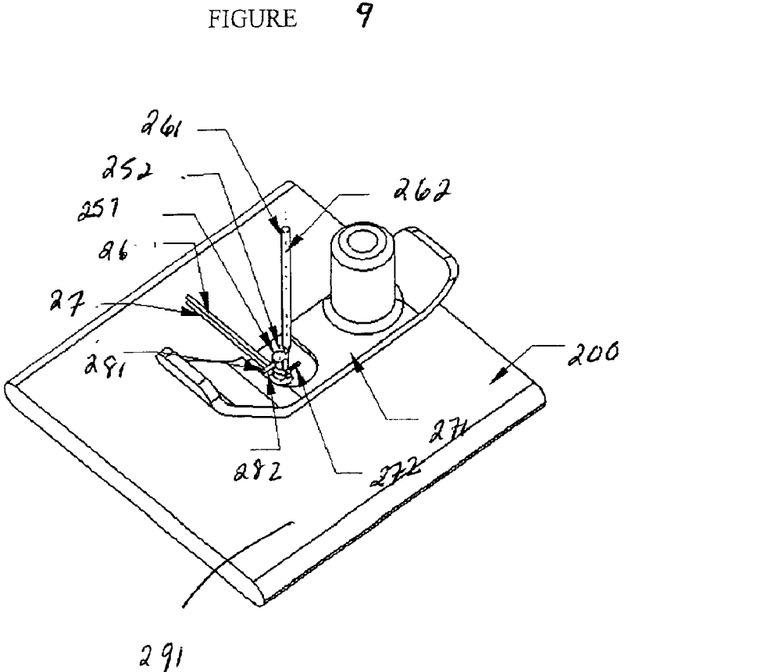
FIG. 9 the perspective view of the sewing apparatus.
Figure 10:
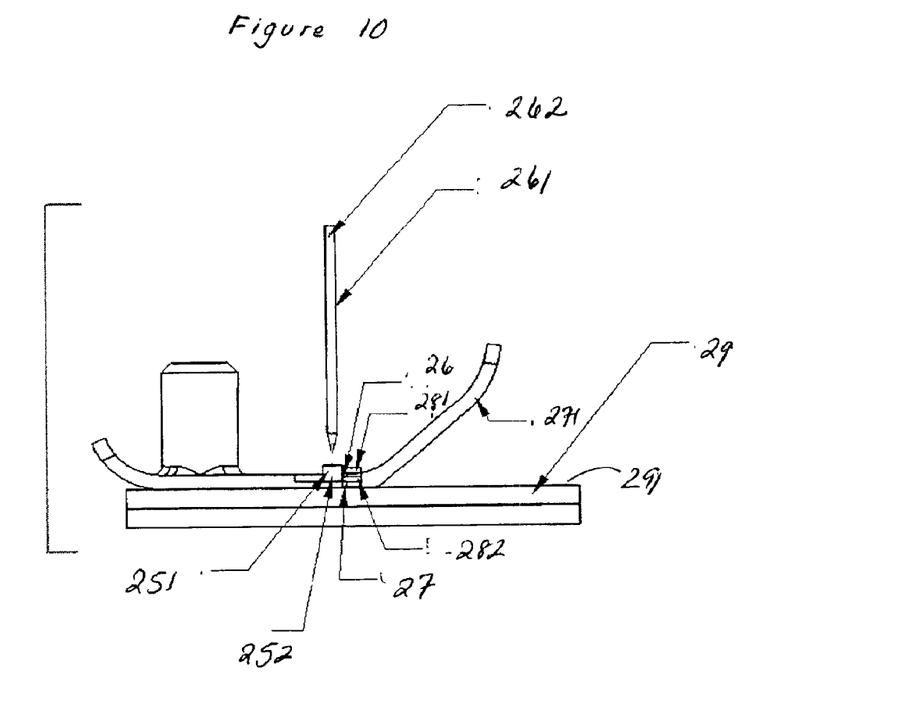
FIG. 10 is the side view of the sewing apparatus.
Figure 11:
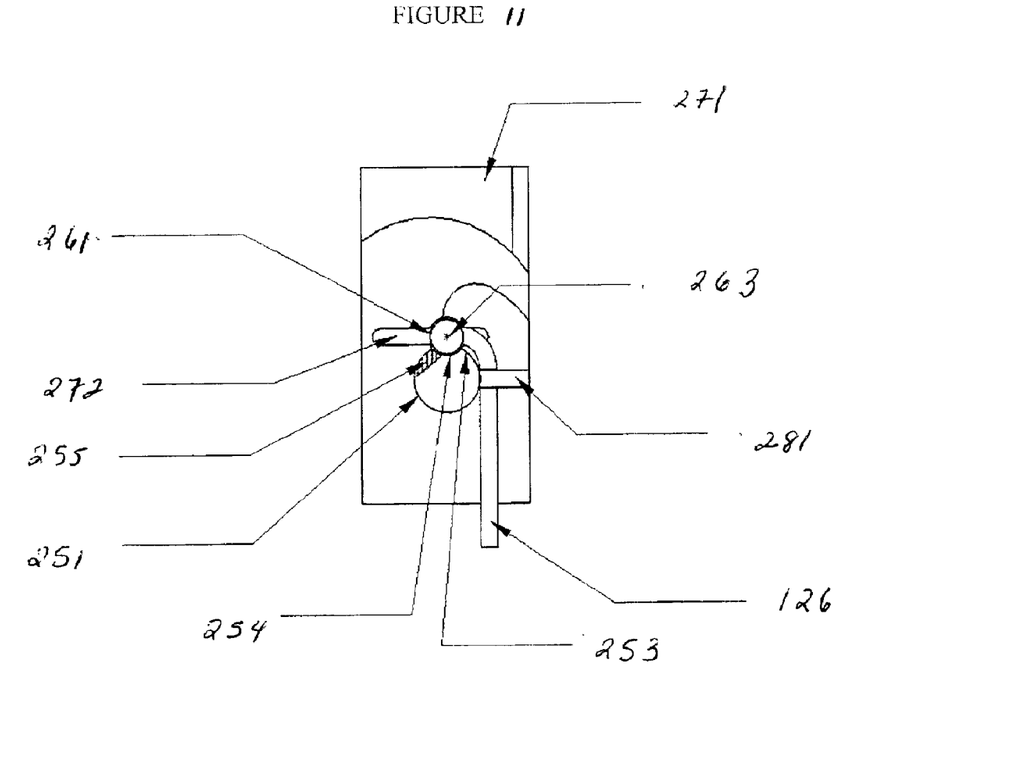
FIG. 11 is the top view of the sewing apparatus.
Figure 12:
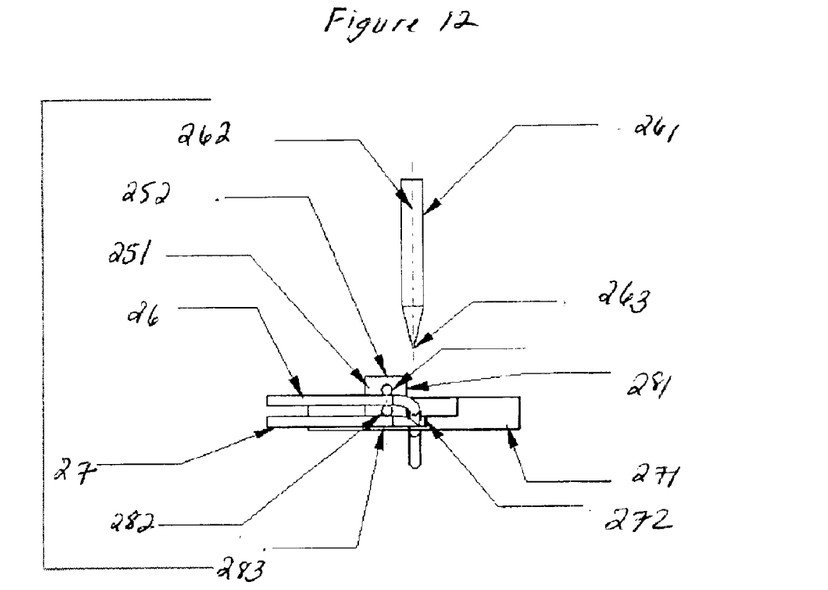
FIG. 12 is the front view of the sewing apparatus.

Because the first cord 26 and the second cord 27 are sewn in two separate parallel planes, the first cord 26 and the second cord 27 are cords which are not twisted while being sewn to a tampon pledget 29. As a result, the first cord 26 and the second cord 27 can be easily tied together into an optional knot 37. (FIG. 8). When a knot 37 is formed, the first cord 26 and the second cord 27 form a loop 38. The loop 38 assists the user in inserting the digital tampon into the woman's vagina by wrapping the loop 38 around one or more fingers and/or the hand of the user which thereby allows greater control to insert the digital tampon. The loop also assists the user in withdrawing the digital tampon by allowing a better grasp of the first cord 26 and/or the second cord 27 when she is ready to remove the tampon from her vagina. The knot 37 also assures that the first cord 26 and the second cord 27 will not separate from one another. Furthermore, the knot 37 also serves to prevent fraying of the first cord 26 and the second cord 27. While a knot 37 is shown, the cords 26 and 27 can be joined together by any means known in the art such as twisting, gluing, bonding, heat sealing, adhering, splicing, etc.

The tail portion 31 should have a length from between about 1 inch to about 6 inches (about 25.4 mm to about 152.4 mm). The first cord 26 and the second cord 27 can be dyed and/or treated with an anti-wicking agent, such as wax, before being attached to the tampon pledget 29. The anti-wicking agent will facilitate and prevent body fluids from wicking along the first cord 26 and the second cord 27 and contacting the inner surface of a woman's undergarment. A dry, clean withdrawal cord is preferred by the user, especially when she is ready to remove the digital tampon from her vagina.

The cords 26 and 27 are sewn to a tampon pledget 29. The digital tampon may be formed from any suitable tampon pledget 29, such as tampon pledgets shown in FIGS. 4–7.

Figure 4:
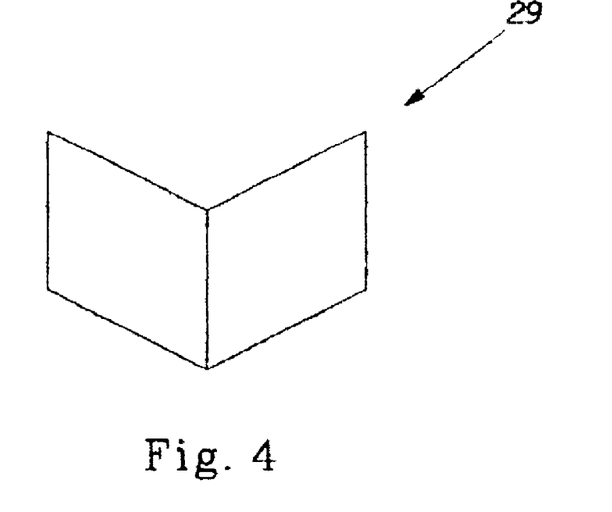
FIG. 4 is a front view of a tampon pledget from which a tampon of the present invention may be made by suitable compression.

The tampon pledget 29 portion of the digital tampon 20 which will be compressed to form the digital tampon may be any suitable shape, size, material, or construction. In the embodiment shown in FIG. 4, tampon pledget 29 is a batt of absorbent material which is a generally "chevron shaped" pad of absorbent material. While a chevron shaped pledget is suitable, the edges of the chevron may be somewhat "rounded off" in order to facilitate high speed manufacturing operations. While the pledget 29 shown in FIG. 4 is generally chevron shaped, other shapes such as trapezoidal, triangular, semicircular, and rectangular shaped are also acceptable.

Figure 5:
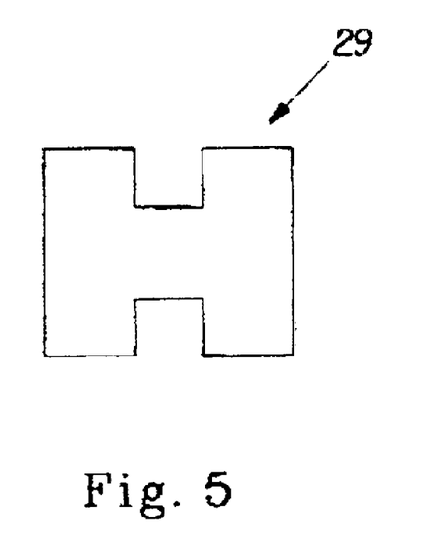
FIG. 5 is a front view of an alternative shape for a tampon pledget.
Figure 6:
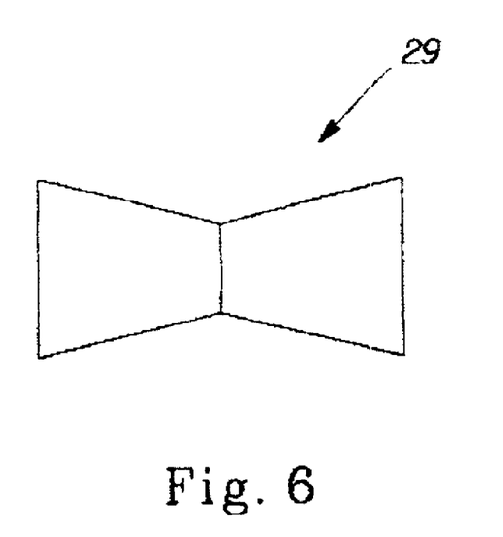
FIG. 6 is a front view of another alternative shape for a tampon pledget.
Figure 7:
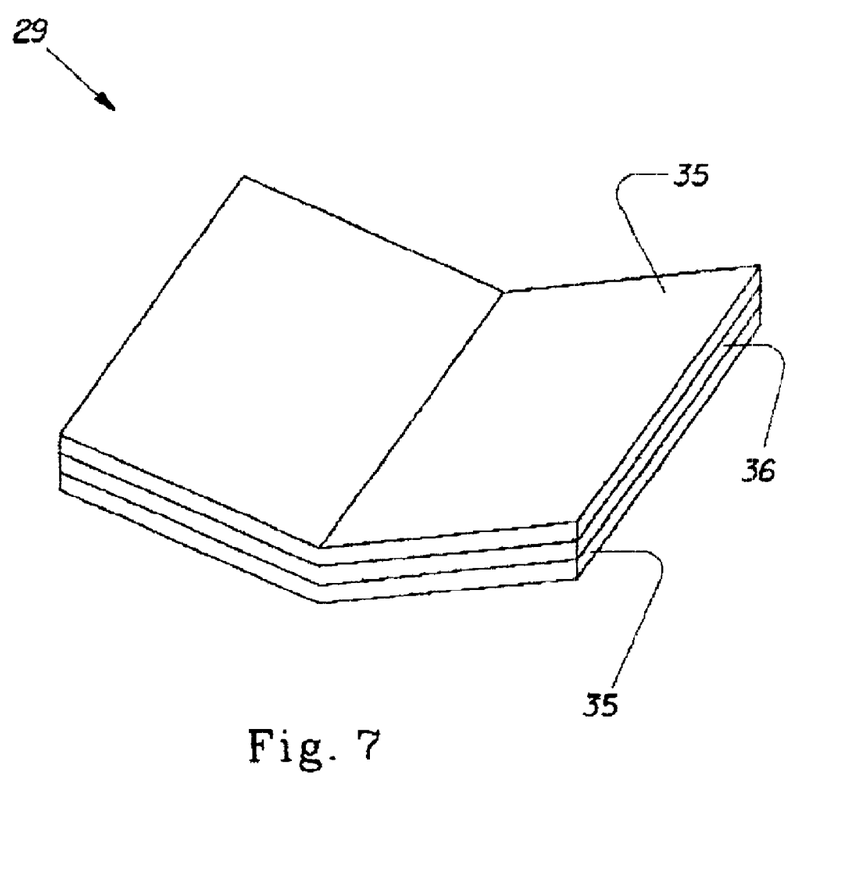
FIG. 7 is a front view of another alternative shape for a tampon pledget.

Other shapes that also tend to produce this variation are also possible. For example, the pledget may be generally "H" shaped 29, such as shown in FIG. 5. A "bow tie" shaped tampon pledget 29 such as is shown in FIG. 6 is also suitable. As an alternative to the shapes of pledgets described above, a tampon pledget 29 of the present invention may have a uniform shape such as a rectangular shape, but may vary in absorbent material density or thickness along the axial extent of the pledget. A more detailed description of liquid-absorbing materials and pledget shapes and dimensions can be found in co-pending case Ser. No. 10/039,979, filed Oct. 24, 2001, entitled "Improved Protection and Comfort Tampon", to Agyapong et al., Docket Number 8758.

In another embodiment, the tampon pledget 29 may be a laminar structure comprised of integral or discrete layers. As is shown more clearly in FIG. 7, the tampon pledget 29 may comprise outer layers 35 and at least one intermediate layer 36 positioned between the outer layers 35. In other embodiments, the pad need not have a layered structure at all. The tampon pledget 29 may comprise a folded structure, may be rolled, may comprise a "petal" structure or any other of the structures, which are known in the art with respect to tampon pledgets.

The tampon pledget 29, and consequently, the resulting digital tampon may be constructed from a wide variety of liquid-absorbing materials commonly used in absorbent articles such as rayon, cotton, or comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss;

foam; tissue including tissue wraps and tissue laminates; or any equivalent material or combinations of materials, or mixtures of these.

The digital tampon and any component thereof may comprise a single material or a combination of materials. Additionally, superabsorbent materials, such as superabsorbent polymers or absorbent gelling materials may be incorporated into the digital tampon. The materials for the digital tampon can be formed into a fabric, web, or batt that is suitable for use in the tampon pledget 29 by any suitable process such as airlaying, carding, wetlaying, hydroentangling, or other known techniques.

C. Apparatus for Making the Digital Tampon of the Present Invention

Referring to FIGS. 9–12, a non-perpendicular turning axis element (hereinafter "NPTA") 251 is introduced to provide accurate cord positioning relative to the needle 261. Defined in reference to the primary motion plane of the sewing needle, the angle between the NPTA element axis 252 and the sewing needle axis 262 is less than 90 degrees. The cord 26 is introduced about the NPTA element 251, where it is rotated into the path of the sewing needle 261 at which point it is attached to the pledget 29, and finally exits under the sewing presser foot 271. The combination of cord take-up from the downstream sewn product, coupled with up-stream cord friction induces tension within the cord 26 that draws the cord 26 sufficiently tight about the circumference of the NPTA element 251. Under this tension, the center of the cord 26 is consistently distanced from the NPTA element axis 252 by the approximate sum of the NPTA element radius plus the cord radius. The sewing needle axis 262 is positioned sufficiently at this distance away from the NPTA element axis 252 so as to allow the sewing needle 261 the ability to penetrate the center of the withdrawal cord 26 passing through the pledget 29 thereby attaching the cord 26 to the pledget 29 with a sewing stitch.

The described apparatus can be expanded to permit the concurrent introduction and sewing of multiple cords such as two cords 26 and 27 stacked atop each other about the NPTA element 251, where they can then be sewn together with the pledget 29. The apparatus to accomplish multiple cord sewing can be achieved by introducing multiple NPTA elements aligned such that the cord will be within the primary axis of needle motion; or an integrated, single NPTA element can be employed to turn and position each cord with each other. In the case of the latter, an example NPTA element 261 employs a single turning surface 253 with sufficient width such that the two cords 26 and 27 can turn side-by-side at the same time with the manufacturer setting the distance between the multiple cords 26 and 27 with optional elevational guide element(s) 281, 282 and 283. Another example of an integrated NPTA element for two or more cords is where the separate turning surfaces exist for one or more of the cords whether the turning surface axes all lie on one plane or if they lie in different planes. For example, one turning surface could be further upstream from another relative to the directional production flow toward the stitching contact point with the needle. Thus an apparatus is provided which better controls the lateral positioning of the cord(s) to allow for more precise alignment between the needle, cord(s) and pledget (or fabric/garment). Even further, the apparatus allows for accurate high speed sewing through multiple cords by accurately positioning them laterally (and elevationally) relative to the cords and the pledget (or fabric/garment).

A guide element which controls the elevation of the cord may also be provided (e.g 281, 282, 283). However, other guide elements can also be utilized to position the incoming cord position with the NPTA element, particularly at the incoming position upstream of the turning surface. The guide element could consist of, but is not limited to circumferential grooves about the NPTA element, guide pins, slats, or eyelets.

A presser foot 271 is provided. The presser foot 271 is a holding element which firmly holds the tampon pledget 29 upon engagement therewith, and maintains its hold through the stitching process. This can be beneficial if the tampon pledget 29 is advanced downstream through a sewing process.

A sewing needle 261 is provided. There is significant variety in the size and shape of available and usable sewing needles. The proposed invention is functional with a wide variety of these and for the purpose of this document, should not be limited to any particular needle embodiment. The sewing needle 261 may be larger in diameter than the cord itself, so long as the needle diameter at the point of entry 263 into the cord 26 is sufficiently small to penetrate the cord 26. An optional clearance groove 254 parallel to the axis of the needle 262 and located about the circumference of the NPTA element 251 can be used to provide clearance for the sewing needle 261 if necessary to penetrate the center of the cord 26 without striking the NPTA element 251. An optional elevational positioning element can be introduced separately or integrally with the NPTA element to assist guiding the cord about the NPTA element. This elevational positioning element could consist of, but is not limited to the addition of circumferential grooves about the NPTA element or upper-lower cord guide pins 281, 282 and 283.

The shape of the needle 261 can be cylindrical so that it comes to a point 263 for easy penetration into the target cord(s), pledget, fabric or garment. The material of the needle is often comprised of a metal or rigid polymer composition. While the main body of the needle 261 typically is a cylinder with a circular cross section, other cross sections are possible such as flat, rectangular, square, elliptical, polygonal, etc.

A materials support surface 291, typically a horizontal sewing support surface, helps to support the workpiece (e.g. tampon pledget and cord) between it and the presser foot 271 as the materials are sewn together.

An optional looper (not shown) is located under the horizontal sewing support surface 291 and is timed with the sewing needle 261 to communicate with the sewing needle 261 to form a sewn stitch through the cord 26 and pledget 29.

D. Method of Making the Digital Tampon of the Present Invention

The method of forming the digital tampon with two cords or cord segments will now be explained with reference to FIGS. 1–8 and to the method FIGS. 9–12.

The summarized steps for the method of sewing a cord (or cords in stacked relation) to a substrate comprise (e.g. tampon pledget) the following steps:

1. drawing a cord from a continuous cord supply;
2. supplying a means to partially resist the feed of the cord which is employed either at the cord supply or downstream of the supply;
3. introducing the cord path into the NPTA element which changes its travel direction as it contacts and moves past the NPTA turning surface—which axis is not perpendicular to the axis of needle motion;
4. optionally positioning the cord between any optionally present elevation guide as part of the NPTA;

5. stacking or layering the cord and substrate prior to or at the point they travel underneath the needle point between a presser foot above and a sewing support surface underneath;
6. drawing the substrate and cord intermittently under the needle by an intermittent drive (e.g. feed dogs, intermittent belts);
7. drawing the cord in concert by the intermittent drive with the means to partially resist the feed of the cord upstream creates a positive draw or tension of the cord from the means to partially resist the feed past the NPTA element to the drawn cord and substrate;
8. stopping the intermittent draw motion;
9. moving the threaded needle through or past the presser foot and penetrating the cord thereby pulling the thread through the cord;
10. continuing the needle downward to penetrate the substrate;
11. pulling the thread through the substrate;
12. engaging the needle with a looper thread as presented by the optional looper mechanism underneath the sewing support surface;
13. reversing the needle direction and moving upward through the substrate and cord and up above the presser foot;
14. activating the intermittent drive and drawing the combined substrate and cord downstream as well as draws more cord from the cord supply and past the NPTA element;
15. repeating the cycle.

If multiple cords are desired, an additional cord can be introduced using a separate NPTA element or an NPTA element that can accommodate an additional cord such that each cord contacts a different part of the turning surface. In the case of two stacked cords, the needle will first penetrate the first cord, then the second cord, and then the substrate. As a further note to the above, the cord/cords and the substrate/substrates can be stacked or layered in any desired order during the sewing such that the first material the needle enters can be either a cord or a substrate. The intermittent drive, needle motion, and optional looper may be powered by any known means of motive force.

The cords 26 and 27 are placed on the NPTA element 251 such that they share the same turning surface 252 but are elevationally separated from each other by the presence of pins 281, 282 and 283. Two pins complete the elevational guide elements for cords 26 and 27, respectively. In this case, the angle between the turning axis of turning surface 252 and the straight needle's axis 262 of needle 261 is 0 degrees. The NPTA element 251 and needle 261 are preferably positioned laterally relative to each other such that the needle point 263 and the needle axis 262 align near or at above the centerline such that the needle 261 will travel with the thread 28 consistently through the two cords 26 and 27 and the pledget 29 underneath.

The cords 26 and 27 are held under tension about the turning surface 252 with the downstream side connected to the pledget 29 via the most recent sewing stitch and the upstream side coming from a supply spool and passing through a friction element before contacting the turning surface 252.

The pledget 29 is introduced intermittently (not shown) into the apparatus first under the front plow of the presser foot 271. The aperture 272 in presser foot 271 provides an opening through which the needle 261 and thread 28 can travel. The pledget 29 is further driven through the process by feed dogs located on the opposite side of the pledget 29 from the presser foot 271 as well as downstream draw induced by nip wheels and belts. The downstream draw of the pledget imparts a drawing force upon the two cords 26 and 27. This drawing affect coupled with an upstream friction element imparts tension into the cords 26 and 27 holding them against the turning surface 252 while also acquiring additional cord as required from their supply reservoirs (spools, boxes, etc., not shown). The cords 26 and 27 are introduced into the apparatus through the respective guide pin pairings 281, 282 and 282, 283 then around the turning surface 252 followed by proceeding underneath the needle point 263.

Alternatively, the pledgets are introduced intermittently. There is an option to continue to sew the two cords 26 and 27 together between the pledgets or draw the cords 26 and 27 out of the line of action of the needle 261. A simple way to execute the latter is to laterally move the NPTA element 251 laterally away from the plane of needle motion via a timed or registered system such that the cords 26 and 27 are removed from the plane of needle motion when no pledget 29 is present and then returned when a new pledget 29 is introduced.

The NPTA element 251 of this example has a relieved cutout area 254 which is present to allow for clearance of the needle body 261 past the NPTA element 251 during its stitching cycle. This is required when the diameter or width of the needle 261 with a centered needle point 263 is wider than the width of the cords 26 and 27 to be sewn, as in this example where the needle diameter is 0.050 inches and the relaxed cord diameters are 0.030 inches. An optional element is an element which can act as a guide for further tension control and/or provide lateral movement positioning control.

A single cord or multiple cords of two or more can be sewn to a pledget. In the case of a single cord, the method still provides superior sewing control for single cord tampon sewing and decorative garment cord sewing.

A key improvement with this invention is that the turning surface axis 252 is non-perpendicular relative to the needle axis 262 or the needle motion plane. For this invention the angle between the NPTA element turning surface axis 252 and the needle axis 262 can range from 0 to 80 degrees.

Also the present method has a nearly parallel turning axis 252, the cord 26 will tend to flatten out within the vertical plane thus narrowing the presented target area for the needle point. This narrowing appears counterintuitive to achieving more accurate stitch positioning control; however, the benefits in lateral position control provided by the NPTA element 251 overcomes this handicap and goes beyond to provide more accurate lateral position control and hence more accurate sewing.

When it comes to the accurate sewing of two or more cords, particularly in a juxtaposed or side-by-side arrangement in the lengthwise dimension, the method of this invention provides accurate lateral position control of each cord relative to each other as well as the needle. A further advantage with the method of this invention is that cords 26 and 27 experience the same travel path such that the cords 26 and 27 will tend to remain stacked atop one another. Looking more closely at the method, the needle 261 starts at the top of the cycle with thread 28 being carried by the needle 261. As the needle 261 advances downward it first penetrates cord 27 approximately through its centerline exits the lower side, then penetrates the top of 26 and exits the bottom side of it where the needle 261 penetrates and then pulls the thread 28 through at least a portion of the pledget 29 where it exits the bottom of pledget 29. The needle 261 then starts its path upward through at least a portion of the three materials until it exits the top of cord 27.

Alternatively, cord 26 could lie in a first cord plane and cord 27 could lie in a second cord plane. The first cord plane and the second cord plane are in parallel planes. The sewing needle can be positioned at an angle from zero to ninety degrees with respect to the first cord plane and the second cord plane.

This method is equally applicably to decorative or reinforcing cord addition of one or more cords to fabrics or garments in the manufacture of textile goods, clothing, coverings, etc. Cords can be in the form of tapes, braids, woven or non-woven strips, elastics, strings, filaments, etc; and, they can be used in the manufacture of clothing, covers, tents, and disposable personal hygiene items such as absorbent products.

What is claimed is:

1. A tampon pledget comprising:

a top end, a bottom end, a first side end, a second side end, and a central portion between said first side end and said second side end, said central portion has a first cord and a second cord, said first cord and said second cord lie in parallel planes, and a thread sewn through said first cord, said second cord, and said pledget.

2. A tampon pledget comprising:

a top end, a bottom end, a first side end, a second side end, and a central portion between said first side end and said second side end, said central portion has a first cord and a second cord, said first cord and said second cord lie in parallel planes, a thread sewn through said first cord, said second cord, and said pledget, said first cord and said second cord having an attached portion and a tail portion, said attached portion lying between said top end and said bottom end, said tail portion extending beyond said bottom end.

3. A tampon pledget of claim 2 wherein the cord diameter is from about 0.05 millimeters to about 0.8 millimeters.

4. The tampon pledget of claim 2 wherein said tail portion is knotted.

5. The tampon pledget of claim 2 wherein said tail portion is glued.

6. The tampon pledget of claim 2 wherein said tail portion is heat sealed.

7. A tampon pledget comprising:

a top end, a bottom end, a first side end, a second side end, and a central portion between said first side end and said second side end, a first cord and a second cord being attached to said central portion, said first cord lies in a first plane and said second cord lie in a second plane, said first plane and said second planes are parallel planes, wherein said first cord and said second cord are sewn to said central portion by a thread.

8. The tampon pledget of claim 7, wherein said first cord and said second cord have an attached portion and a tail portion, said attached portion lying between said top end and said bottom end, said tail portion extending beyond said bottom end.

9. The tampon pledget of claim 8, wherein said tail portion is knotted.

10. The tampon pledget of claim 8, wherein said tail portion is glued.

\* \* \* \* \*